United States Patent
Wu et al.

(10) Patent No.: US 12,024,773 B2
(45) Date of Patent: Jul. 2, 2024

(54) NON-STICK COATING AND ITS MANUFACTURING METHOD

(71) Applicant: Picosun Oy, Espoo (FI)

(72) Inventors: Xiaopeng Wu, Masala (FI); Juhana Kostamo, Masala (FI); Niku Oksala, Masala (FI)

(73) Assignee: PICOSUN OY, Espoo (FI)

( * ) Notice: Subject to any disclaimer, the term of this patent is extended or adjusted under 35 U.S.C. 154(b) by 116 days.

(21) Appl. No.: 16/832,187

(22) Filed: Mar. 27, 2020

(65) Prior Publication Data

US 2020/0308702 A1  Oct. 1, 2020

Related U.S. Application Data

(60) Provisional application No. 62/825,984, filed on Mar. 29, 2019.

(51) Int. Cl.
*C23C 16/455* (2006.01)
*A61F 2/04* (2013.01)
(Continued)

(52) U.S. Cl.
CPC .......... *C23C 16/45555* (2013.01); *A61F 2/04* (2013.01); *C23C 16/32* (2013.01); *C23C 16/4583* (2013.01); *A61F 2002/044* (2013.01); *A61F 2210/0004* (2013.01); *A61F 2210/0076* (2013.01); *A61F 2240/001* (2013.01)

(58) Field of Classification Search
CPC .......... A61K 31/70; A61K 31/66; D04H 3/00; C23C 16/44; C23C 16/00; C23C 16/34; A61F 2/82; A61F 2/06; A61F 2/66; A61F 2/00; A61M 25/00; A61N 1/05;
(Continued)

(56) References Cited

U.S. PATENT DOCUMENTS 6,520,923 B1 * 2/2003 Jalisi .................... A61M 25/09
600/585
6,784,083 B1 * 8/2004 Gealy ............... C23C 16/45544
438/584

(Continued)

FOREIGN PATENT DOCUMENTS

EP  2456481 B1  11/2016

OTHER PUBLICATIONS

Volenec et al., The challenges: Stent materials from the perspective of the manufacturer, Jun. 2013, International Journal of Gastrointestinal Intervention, vol. 5, No. 2, pp. 98-104 (Year: 2013).*

(Continued)

*Primary Examiner* — Dah-Wei D. Yuan
*Assistant Examiner* — Andrew J Bowman
(74) *Attorney, Agent, or Firm* — Espatent Oy

(57) ABSTRACT

A medical stent, including a squeezable and expandable tubular wire mesh and an anti-sticking atomic layer deposition coating deposited on surfaces of the wire mesh. A method for manufacturing a medical stent, including taking a squeezable and expandable (i.e., deformable) tubular wire mesh, and depositing an anti-sticking atomic layer deposition coating on surfaces of the wire mesh to prevent the wire mesh from being stuck with itself when expanding from a squeezed form to a fully expanded form.

10 Claims, 2 Drawing Sheets

(51) Int. Cl.
*C23C 16/32* (2006.01)
*C23C 16/458* (2006.01)

(58) Field of Classification Search
CPC ... B32B 5/16; A61L 27/54; A61L 2/03; A61L 2/07; A61L 2/20
See application file for complete search history.

(56) References Cited

U.S. PATENT DOCUMENTS

| | | | |
|---|---|---|---|
| 6,905,547 B1* | 6/2005 | Londergan | C23C 16/45544 118/715 |
| 8,833,430 B2 | 9/2014 | Aizenberg et al. | |
| 9,155,637 B2 | 10/2015 | Mendelson et al. | |
| 2003/0116087 A1* | 6/2003 | Nguyen | C23C 16/45565 438/791 |
| 2003/0130228 A1* | 7/2003 | Chen | A61K 31/7072 514/50 |
| 2005/0221072 A1* | 10/2005 | Dubrow | A61L 27/3821 428/292.1 |
| 2008/0069854 A1* | 3/2008 | Xiao | A61L 27/306 424/423 |
| 2008/0071352 A1* | 3/2008 | Weber | A61L 31/16 623/1.42 |
| 2012/0177910 A1* | 7/2012 | Weber | A61L 31/088 977/773 |
| 2013/0116682 A1 | 5/2013 | Koo et al. | |
| 2013/0296678 A1* | 11/2013 | Larsen | A61N 1/05 607/116 |
| 2018/0207325 A1 | 7/2018 | Hasan | |
| 2018/0362875 A1 | 12/2018 | Aizenberg et al. | |

OTHER PUBLICATIONS

Gegenschatz-Schmid, Acta Biomaterialia, Reduced thrombogenicity of surface-treated Nitinol implants steered by altered protein adsorption, Elsevier, Apr. 26, 2021,15 (330-335), Science Direct, Switzerland.

Hsi-Yi Yeh, Bioactivity and Platelet Adhesion Study of a Human Thrombomodulin-Immobilized Nitinol Surface, Journals of Biomaterials Science, Polymer Edition, 2009, 807-819, vol. 20, online.

K. Song, A superhydrophilic nitinol shape memory alloy with enhanced anti-biofouling and anti-corrosion properties, The Journal of Bioadhesion and Biofilm Research (Biofouling), 2016,535-545, vol. 32, Online.

Thierry, Blood Compatibility of Nitinol Compared to Stainless Steel, www.nitinol.com, 2000, 285-290, Fremont California.

* cited by examiner

NON-STICK COATING AND ITS MANUFACTURING METHOD

FIELD

The aspects of the disclosed embodiments generally relate to coatings and their manufacturing methods.

BACKGROUND

This section illustrates useful background information without admission of any technique described herein representative of the state of the art.

Medical stents are used widely inside arteries and veins to prevent recoil of stenosis to allow for unaltered blood flow and minimize potential pressure drop after percutaneous transluminal angioplasty or to cover/seal arterial or venous injuries or spontaneous ruptures to prevent hemorrhage (vascular surgery, cardiology, neurovascular interventions) and as a crucial part of endografts such as arterial endografts used in the treatment of arterial aneurysms (vascular surgery) and endovascular heart valves (cardiology and thoracic surgery) intended to treat valvular dysfunction (stenosis or regurgitation). In addition to these, stents are used to dilate stenoses of the esophagus (gastroenterology) to allow unaltered intake of food despite strictures caused by cancer or inflammation, bile ducts to allow flow of bile and other parts of the gastrointestinal tract (gastroenterology) and also stenoses in the ureters or urethra (urology).

Stents are inserted using a special catheter (around which the stent is compressed during the manufacturing process) guided through the stenosed or damaged area over a guidewire and then either released or released and balloon dilated depending on the characteristics of the stent. During stent release, it is possible that the stent does not return to its intended original shape due to stiction. This may lead to a situation, in which the stent has to be removed because the stent causes disturbed flow at the site of insertion. Ultimately, this may require open surgical procedure. After insertion, the stent should remain intact and allow for unobstructed flow. However, the insertion of stent induces an inflammatory response and alteration of wall biomechanics predisposing the area to re-stenosis and failure of the treatment by several mechanisms (intimal hyperplasia in arteries, mucosal hypertrophy in gastrointestinal tract, epithelial hyperplasia in the bile duct, ureters and urethra).

SUMMARY

It is an object of certain embodiments of the present disclosure to alleviate the problem mentioned in the background section.

According to a first example aspect of the disclosed embodiments there is provided a method, comprising:
  manufacturing a medical stent, said manufacturing comprising:
  taking a deformable tubular wire mesh; and
  depositing an anti-sticking coating by ALD or MLD on surfaces of the wire mesh in a vertical flow reaction chamber.

In certain embodiments, the method comprises:
covering the wire mesh coated by the anti-sticking coating by a flexible tube.

In certain embodiments, the wires of the wire mesh are plastic wires so that said depositing comprises depositing said anti-sticking coating on surfaces of the plastic wires.

In certain embodiments, the method comprises:
manufacturing a biodegradable stent.

In certain embodiments, the method comprises:
depositing a biodegradable anti-sticking coating.

In certain embodiments, said depositing comprises depositing a carbide coating. In certain embodiments, the method comprises depositing a carbide coating by ALD.

In certain embodiments, the material of the anti-sticking coating is selected from a group consisting of:
  TiC;
  TaC; and
  WC.

In certain embodiments, the method comprises depositing an MLD coating selected from a group consisting of:
  alucone;
  titanicone; and
  zincone.

In certain embodiments, the method comprises:
  coating the anti-sticking coating by propylthiouracil material.

In certain embodiments, the method comprises manufacturing of a gastric stent.

In certain embodiments, said vertical flow is implemented by a reactive chemical inlet in a top section of the reaction chamber and a pump fore-line in a bottom section of the reaction chamber.

In certain embodiments, the method comprises:
  supporting the medical stent by a substrate support from below during deposition; and
  causing a reactive chemical flow into an interior side of the tubular wire mesh from above, the flow further exiting the interior side and by-passing the substrate support maintaining a generally downward flow direction.

In certain embodiments, the substrate support is gas-permeable allowing a top-to-bottom flow of reactive chemical through the reaction chamber extending all the way from the inlet to fore-line. In certain embodiments, the substrate support is porous, or comprises pores.

In certain embodiments, the method comprises:
  providing a gas-permeable substrate support, having through holes, underneath the medical stent allowing reactive chemical exiting the interior of the tubular wire mesh to continue via said through holes downwards towards a pump fore-line positioned at a bottom section of the reaction chamber.

According to a second example aspect of the present disclosure there is provided a medical stent manufactured by the method of the first aspect or any of its embodiments, comprising:
  a squeezable and expandable tubular wire mesh; and
  an anti-sticking ALD or MLD coating deposited on surfaces of the wire mesh.

In certain embodiments, the stent comprises the anti-sticking coating to aid the return of a wire mesh structure of the stent into its original form once positioned.

In certain embodiments, the wire mesh coated by the coating is covered by a flexible tubular item.

According to a third example aspect of the disclosed embodiments there is provided a medical stent, comprising:
  a squeezable and expandable tubular wire mesh;
  an anti-sticking atomic layer deposition coating deposited on surfaces of the wire mesh.

In certain embodiments, the wires of the wire mesh are metal wires, or plastic wires.

In certain embodiments, the wire mesh coated by the coating is covered by a flexible tubular item. Accordingly, in certain embodiments the stent comprises a flexible tube covering the wire mesh. In certain embodiments, the wire mesh coated by the coating is covered by a flexible tube made of cloth material or Teflon.

In certain embodiments, the material of the coating is selected from a group consisting of:
$Al_2O_3$;
$TiO_2$;
TiC;
TaC; and
WC.

According to a fourth example aspect of the disclosed embodiments there is provided a method for manufacturing the medical stent of the third aspect or any of its embodiments.

Accordingly, there is provided a method, comprising:
manufacturing a medical stent, the manufacturing comprising:
taking a squeezable and expandable (i.e., deformable) tubular wire mesh; and
depositing an anti-sticking atomic layer deposition, ALD, coating on surfaces of the wire mesh.

In certain embodiments, a purpose of the coating is to prevent the wire mesh from being stuck with itself when expanding from a squeezed form to an expanded (or fully expanded) form.

The stent in disclosed aspects may be of the following types: 1) bare wire mesh stent, 2) bare wire mesh stent with drug eluting coating, 3) biodegradable stent and 4) tubular stent comprising of wire mesh stent inside a flexible tube made out of cloth material or teflon.

The anti-sticking (or non-stick) atomic layer deposition, ALD or MLD, coating is to prevent sticking of the stent when expanding. In certain embodiments, the stent is in its original form when expanded, and in a squeezed form when moved into its correct placement (destination) within a human body. Accordingly, in certain embodiments, the tubular wire mesh is squeezable from its original expanded form into a squeezed form for transport. In certain embodiments, the anti-sticking coating is to aid the return of the wire mesh structure into its original form (from the squeezed form) while in its destination (so that the wires of the wire mesh structure do not get stuck with each other during the act of expanding thus preventing the stent from returning into its original form).

Advantageously with a specific coating with a given material, the stent inner lumen remains open for a maximal time-period, while the outer surface integrates with the surroundings. Yet advantageously, in case of vascular (or arterial) stents, the coated inner luminal surface prevents adherence of platelets and formation of blood clots otherwise obstructing the stent and also prevents intimal hyperplasia after a smooth endothelial lining has completed.

A reference is made to the preceding as to the types, structures, insertion methods, and usage scenarios of medical stents. Accordingly, the medical stents herein may be of any of the types, and contain any of the structures disclosed in the preceding. Furthermore, the medical stents herein may be configured for any of the insertion methods, and usage scenarios disclosed in the preceding.

Different non-binding example aspects and embodiments have been presented in the foregoing. The above embodiments and embodiments described later in this description are used to explain selected aspects or steps that may be utilized in implementations of the present disclosure. It should be appreciated that corresponding embodiments apply to other example aspects as well. Any appropriate combinations of the embodiments can be formed.

BRIEF DESCRIPTION OF THE DRAWINGS

The aspects of the disclosed embodiments will now be described, by way of example only, with reference to the accompanying drawings, in which.

DETAILED DESCRIPTION

Figure 1A:
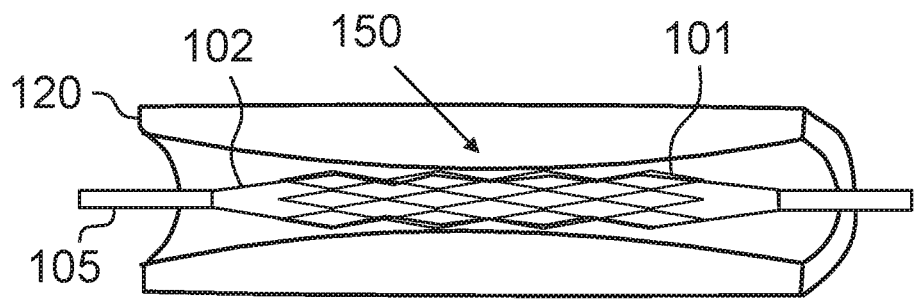
FIGS. 1a-1c show a medical stent and its insertion into its destination in accordance with certain embodiments.

In the following description, Atomic Layer Deposition (ALD) technology is used as an example.

The basics of an ALD growth mechanism are known to a skilled person. ALD is a special chemical deposition method based on the sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: MLD (Molecular Layer Deposition), plasma-assisted ALD, for example PEALD (Plasma Enhanced Atomic Layer Deposition) and photon-enhanced Atomic Layer Deposition (known also as photo-ALD or flash enhanced ALD).

A basic ALD deposition cycle consists of four sequential steps: pulse A, purge A, pulse B and purge B. Pulse A consists of a first precursor vapor and pulse B of another precursor vapor. Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapor pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

Stents are inserted, e.g., into the esophagus or damaged arteries, and then expanded to open the clogged artery or esophagus, and restore the blood or nutrition flow through the artery or esophagus, respectively. The purpose of a vascular stent is to reduce the pressure drop of the blood flow through the damaged artery section and thus enable proper blood stream to the organ the artery is feeding. The "gastric stent" in turn helps the patient to take nutrition through the stomach tube which was narrowed down due to some disease, e.g., cancer.

The stents herein may be bare wire mesh stents, or tube stents comprising of wire mesh stent inside a flexible tube. The tube may be made of cloth material or, e.g., Teflon.

Figure 1B:
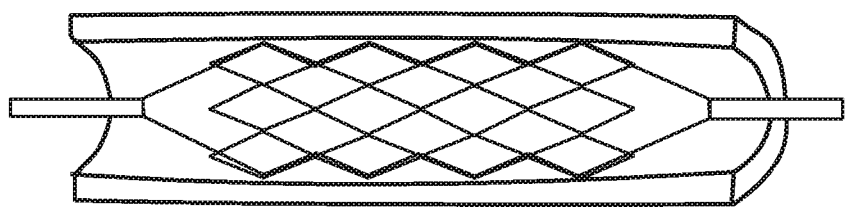
Figure 1C:
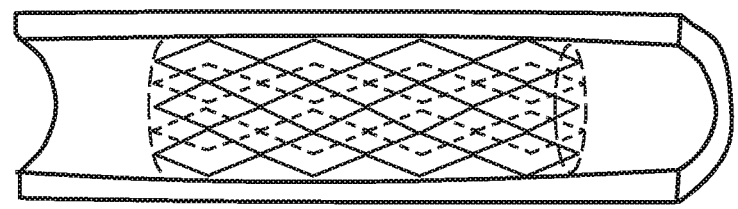

FIGS. 1a-1c show a medical stent and its positioning into its destination in accordance with certain embodiments. The stent is squeezed in when moved in the tube 120 in question (such as an artery, or esophagus, etc. depending on the embodiment) within a human body. When reaching the right position (damaged section 150), the stent is expanded (the stent is inserted using a catheter 105 around which the stent is compressed). The stent comprises a squeezable and expandable tubular wire mesh 101, and an anti-sticking atomic layer deposition (ALD) coating deposited on surfaces of the wire mesh 101 in a reaction chamber of a deposition reaction. An inflatable balloon 102 may be provided under the mesh 101 to aid expanding of the mesh 101 (see FIG. 1b with the balloon 102 inflated). The balloon 102 and catheter 105 are subsequently removed, but the expanded mesh 101 remains at the damaged area 150 and supports the tube 120 as desired.

The anti-sticking (or non-stick) ALD coating is to prevent sticking of the stent when expanding. In certain embodiments, the stent is in its original form when expanded, and in a squeezed form when moved into its correct placement (destination) within a human body. Accordingly, in certain embodiments, the tubular wire mesh is squeezable from its original expanded form into a squeezed form for transport. In certain embodiments, the anti-sticking coating is to aid the return of the wire mesh structure into its original form (from the squeezed form) while in its destination (so that the wires of the wire mesh structure do not get stuck with each other during the act of expanding thus preventing the stent from returning into its original form).

In certain embodiments, the wires of the wire mesh are metal wires, or plastic wires.

In certain embodiments, the wire mesh coated by the coating is covered by a flexible tubular item. Accordingly, in certain embodiments the stent comprises a flexible tube covering the wire mesh. In certain embodiments, the wire mesh coated by the coating is covered by a flexible tube made of cloth material or Teflon.

In certain embodiments, the material of the coating is selected from a group consisting of: $Al_2O_3$, $TiO_2$, TiC, TaC, and WC.

In certain embodiments, the stent comprises a mesh made, e.g., of metal coated by a releasable drug, e.g., PTU (Propylthiouracil) material. The mesh is first coated by the non-stick ALD layer, and thereafter the releasable drug is added. The stent is compressed before use. Once positioned, the stent is released. The non-stick ALD layer aids in returning the mesh back to its original shape when positioned.

In accordance with a manufacturing method of a medical stent, a squeezable and expandable (i.e., deformable) tubular wire mesh is first taken, and an anti-sticking atomic layer deposition coating is deposited on surfaces of the wire mesh, to prevent the wire mesh from being stuck with itself when expanding from a squeezed form to a fully expanded form.

Figure 2:
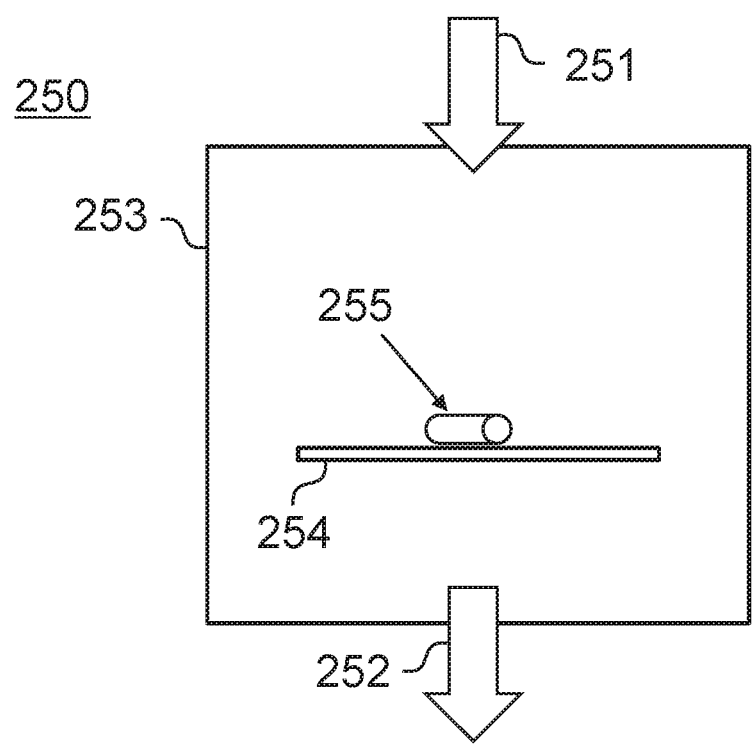
FIG. 2 shows a substrate processing apparatus in accordance with certain embodiments.

FIG. 2 shows a substrate processing apparatus (or deposition reactor) 250 in accordance with certain embodiments. The apparatus 250 comprises a reaction chamber 253, and at least one coating material inlet 251 to the reaction chamber 253. The apparatus 250 further comprises a fore-line 252 to a pump (for exhaust of gases). In the embodiment shown in FIG. 2, the inlet 251 for the coating material (or reactive chemical) is positioned in a top section of the reaction chamber 253 and the fore-line 252 in a bottom section, the general flow direction within the reaction chamber 253 thus being vertical (downwards).

A substrate support 254 supports the stent 255 (or its tubular wire mesh) loaded into the reaction chamber 253 for example from a side. The stent 255 is processed by ALD to produce a coating with a pre-determined number of layers of pre-determined material(s).

In certain embodiments, the substrate support 254 is gas-permeable allowing a top-to-bottom flow of reactive chemical through the reaction chamber 253 extending all the way from the inlet 251 to fore-line 252. In certain embodiments, the substrate support 254 is provided as a gas-permeable substrate support, having through holes, underneath the medical stent allowing reactive chemical exiting the interior of the tubular wire mesh to continue via said through holes downwards towards the pump fore-line 252 positioned at a bottom section of the reaction chamber 253. In certain embodiments, the substrate support 254 is porous, or comprises pores.

The preceding description generally applies various types of medical stents.

Without limiting the scope and interpretation of the patent claims, certain technical effects of one or more of the example embodiments disclosed herein are listed in the following. A technical effect is aiding a medical stent to recover its original form once positioned on a damaged section within a human body. A further technical effect is optimal flow geometry. A further technical effect is providing biodegradable stents with an anti-sticking coating. A further technical effect is providing a stent with a biodegradable coating.

The foregoing description has provided by way of non-limiting examples of particular implementations and embodiments of the present disclosure a full and informative description of the best mode presently contemplated by the inventors for carrying out the present disclosure. It is however clear to a person skilled in the art that the present disclosure is not restricted to details of the embodiments presented above, but that it can be implemented in other embodiments using equivalent means without deviating from the characteristics of the present disclosure.

Furthermore, some of the features of the above-disclosed embodiments of this present disclosure may be used to advantage without the corresponding use of other features. As such, the foregoing description should be considered as merely illustrative of the principles of the present disclosure, and not in limitation thereof. Hence, the scope of the present disclosure is only restricted by the appended patent claims.

The invention claimed is:

1. A method, comprising:
   manufacturing a medical stent, said manufacturing comprising:
   taking a deformable tubular plastic wire mesh comprising plastic wires;
   preventing the plastic wires from sticking to each other by depositing an anti-sticking coating by ALD (Atomic Layer Deposition) or MLD (Molecular Layer Deposition) on surfaces of the plastic wires of the plastic wire mesh in a vertical flow reaction chamber; and
   providing a gas-permeable substrate support, having through holes, underneath the medical stent allowing reactive chemical exiting the interior of the tubular plastic wire mesh to continue via said through holes downwards towards a pump fore-line positioned at a bottom section of the reaction chamber.

2. The method of claim 1, comprising:
covering the plastic wire mesh coated by the anti-sticking coating by a flexible tube.

3. The method of claim 1, comprising:
manufacturing a biodegradable stent.

4. The method of claim 1, comprising:
depositing a biodegradable anti-sticking coating.

5. The method of claim 1, wherein said depositing comprises depositing a carbide coating.

6. The method of claim 5, wherein the material of the anti-sticking coating is selected from a group consisting of:
TiC;
TaC; and
WC.

7. The method of claim 1, comprising:
coating the anti-sticking coating by propylthiouracil material.

8. The method of claim 1, comprising manufacturing of a gastric stent.

9. The method of claim 1, wherein said vertical flow is implemented by a reactive chemical inlet in a top section of the reaction chamber and a pump fore-line in a bottom section of the reaction chamber.

10. The method of claim 1, comprising:
supporting the medical stent by a substrate support from below during deposition; and
causing a reactive chemical flow into an interior side of the tubular plastic wire mesh from above, the flow further exiting the interior side and by-passing the substrate support maintaining a generally downward flow direction.

* * * * *